United States Patent [19]

Bulteau et al.

[11] 4,161,532

[45] Jul. 17, 1979

[54] N-(1'-ETHYL-2'-OXO-5'-PYRROLIDINYL-METHYL) BENZAMIDE COMPOUNDS AND DERIVATIVES, METHOD OF PREPARATION AND PHARMACEUTICAL PREPARATIONS

[75] Inventors: Gérard Bulteau, Paris; Jacques Acher, Itteville; Jean C. Monier, Lardy, all of France

[73] Assignee: Societe d'Etudes Scientifiques et Industrielles de l'Ile de France, Paris, France

[21] Appl. No.: 896,126

[22] Filed: Apr. 14, 1978

[30] Foreign Application Priority Data

Apr. 15, 1977 [FR] France .................................. 77 11644

[51] Int. Cl.² .................... C07D 207/20; A61K 31/40
[52] U.S. Cl. ................................ 424/274; 260/326.45

[58] Field of Search .................. 260/326.45; 424/274; 429/326.47

[56] References Cited

U.S. PATENT DOCUMENTS

| | | | |
|---|---|---|---|
| 3,862,139 | 1/1975 | Podesva et al. | 260/326.47 |
| 3,891,671 | 6/1975 | Thominet | 424/274 |
| 3,923,829 | 12/1975 | Denzler | 260/326.47 |
| 4,021,567 | 5/1977 | Kaplan et al. | 424/274 |
| 4,029,673 | 6/1977 | Bulteau et al. | 260/326.47 |

*Primary Examiner*—Donald G. Daus
*Assistant Examiner*—Mary Lee
*Attorney, Agent, or Firm*—John C. Smith, Jr.

[57] ABSTRACT

Novel substituted N-(1'-ethyl-2'-oxo-5'-pyrrolidinylmethyl) benzamide compounds and derivatives thereof are disclosed. The compounds have psychotropic properties and may be used in pharmaceutical compositions as behavior modifiers.

10 Claims, No Drawings

N-(1'-ETHYL-2'-OXO-5'-PYRROLIDINYL-METHYL) BENZAMIDE COMPOUNDS AND DERIVATIVES, METHOD OF PREPARATION AND PHARMACEUTICAL PREPARATIONS

This invention relates to novel substituted N-(1'-ethyl-2'-oxo-5'-pyrrolidinylmethyl) benzamide compounds, pharmacologically acceptable organic or inorganic acid addition salts thereof, quaternary ammonium salts thereof, N-oxides thereof and optical isomers thereof; a process for preparing these compounds and pharmaceutical preparations containing these compounds which have psychotropic properties and are useful as behavior modifiers.

The structural formula of the substituted N-(1'-ethyl-2'-oxo-5'-pyrrolidinylmethyl) benzamide compounds of the present invention is as follows:

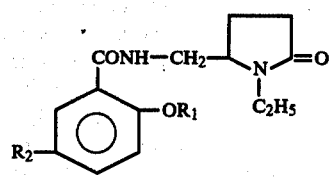

wherein:
$R_1$ is hydrogen or methyl and
$R_2$ is hydrogen or sulfamoyl.

The preferred benzamide compounds of the present invention are N-(1'-ethyl-2'-oxo-5'-pyrrolidinylmethyl)-2-methoxy-5-sulfamoyl-benzamide and N-(1'-ethyl-2'-oxo-5'-pyrrolidinylmethyl)-2-hydroxy-5-sulfamoyl-benzamide.

The pharmacologically acceptable acid addition salts of the benzamide compounds may be prepared by reacting the benzamide compounds with a pharmaceutically acceptable inorganic or organic acid such as hydrochloric acid, hydrobromic acid, sulfuric acid, phosphoric acid, oxalic acid, acetic acid, tartaric acid, citric acid or methane sulfonic acid.

The quarternary ammonium salts of the benzamide compounds may be produced by reacting the benzamide compound with an alkyl sulfate or alkyl halide.

The benzamide compounds and their derivatives are useful in psychotropic pharmaceutical compositions. The pharmaceutical comositions, when administered to a patient, have been found to serve as behavior modifiers. The pharmaceutical compositions include a pharmaceutically acceptable support and may be in the form of capsules, syrup, potable or injectable solutions, tablets, soluble powders, etc.

The benzamide compounds of the invention may be prepared by reacting a compound of the following formula:

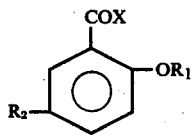

wherein
x is a hydroxyl radical, a hydrogen atom or an organic residue,
$R_1$ is hydrogen or methyl and
$R_2$ is hydrogen or sulfamoyl with a racemic amine of the following formula:

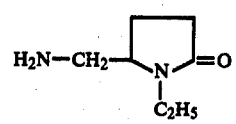

an optical isomer of the racemic amine or a reactive derivative of the racemic amine.

The organic residue of the initial compound (II) must be capable of forming an acid reactive derivative. Examples include lower alkyl esters such as methyl, ethyl, propyl, butyl, isobutyl, pentyl and isopentyl; reactive acid esters such as methoxymethyl ester, cyanomethyl ester, substituted or unsubstituted aromatic esters and N-hydroximide esters; acid azides; acid hydrazides; symmetrical anhydrides; mixed anhydrides such as those formed from carbonic acid esters and haloform esters; azolides such as triazolides, tetrazolides, imidazolides, substituted ω-trihaloacetophenones; substituted α-oxobenzeneacetonitriles; benzamides substituted on the ring and the compound of the general formula:

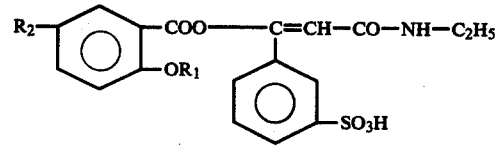

wherein
$R_1$ is hydrogen or methyl and
$R_2$ is hydrogen or sulfamoyl
and which is formed from 2-(hydroxy or methoxy)-5-sulfamoyl benzoic acid and an isoxazolium salt.

The racemic amine (III) may be in the form of a reactive derivative. Examples of suitable reactive derivatives include the reaction products of the amine with phosphorus chlorides; phosphorus oxychloride; dialkyl, diaryl or orthophenylene chlorophosphates; alkyl or aryl dichlorophosphites; 1-ethyl-2-oxo-5-aminomethyl-pyrrodine isothiocyanate; N-(1-ethyl-2-oxo-5-pyrrolidylmethyl) sulfamides (symmetrical or unsymmetrical); N,N' bis-(1-ethyl-2-oxo-5-pyrrolidylmethyl) urea and N-(ethyl-2-oxo-5-pyrrolidylmethyl) enamine.

The reactive derivative of the racemic amine may be reacted with the acid in situ or after preliminary isolation.

The reaction of the free acid and free amine may be carried out in the presence of a condensing agent as for example silicon tetrachloride, phosphoric anhydride, a carbodiimide such as dichloohexyl carbodiimide or an alkoxyacetylene such as methoxy or ethoxy acetylene.

The amidification reaction may be carried out either in the presence of or absence of a solvent. Suitable solvents, which must be inert with respect to the amidification reaction, include, for example, polyol alcohols, benzene, toluene, dioxane, chloroform and the dimethyl ether of diethyleneglycol. Alternatively, an excess of the racemic amine may be used as the solvent. Preferably, the reaction mixture is maintained at an elevated temperature during reaction; as for example, the boiling point of the solvent. However, the amidification reaction may be carried out at ambient temperature.

To further illustrate the features of the present invention some embodiments will be described hereinafter, it being understood that these are not limiting.

EXAMPLE 1

N-(1'-ethyl-2'-oxo-5'-pyrrolidinylmethyl)-2-methoxy-5-sulfamoyl benzamide 6 g (0.042 mole) of 1-ethyl-2-oxo-5-aminomethylpyrrolidine, 5 g (0.050 mole) of triethylamine and 30 ml of methyl ethyl ketone were introduced into a 250 ml flask provided with a therometer, stirrer, and dropping funnel. While the temperature was maintained at 15°–20° C. a solution of 10 g (0.040 mole) of 2-methoxy-5-sulfamoyl benzoyl chloride and 120 ml of methyl ethyl ketone was added drop by drop. An abundant white precipitate was formed immediately. Reaction was allowed to continue for 30 minutes at ambient temperature after which the precipitated crystals were filtered, washed with water, dilute ammonia, and again with water and then dried in an oven at 50° C. 6.8 g of N(1'-ethyl-2'-oxo-5'-pyrrolidinylmethyl)-2-methoxy-5-sulfamoyl benzamide were obtained (M.P.: 231° C.; Yield: 47.9%).

EXAMPLE 2

N-(1'-ethyl-2'-oxo-5'-pyrrolidinylmethyl)-2-hydroxy-5-sulfamoyl benzamide 6.1 g (0.025 mole) of 2-hydroxy-5-sulfamoyl ethyl benzoate, 40 ml of butanol, 3.7 g (0.026 mole) of 1-ethyl-2-oxo-5-aminomethylpyrrolidine and 10 ml of triethylamine were introduced into a 250 ml flask equipped with a stirrer and condenser. The mixture was heated for 7 hours with reflux and allowed to stand overnight. A white precipitate was formed which was filtered and dissolved in 40 ml of water after which 0.8 ml of acetic acid was added. An oil, which crystallized, was obtained. The crystals were filtered, washed with water and dried in an oven at 50° C. 4.3 g of N-(1'-ethyl-2'-oxo-5' pyrrolidinylmethyl)-2-hydroxy-5-sulfamoyl benzamide were obtained (M.P.: 209° C.; Yield: 46.6%). The benzamide was then recrystallized in 100 ml of methanol resulting in 3.2 g of crystals (M.P.: 211° C.; Yield: 34.7%).

The following examples are representative pharmaceutical preparations for the treatment of patients:

EXAMPLE 3

150 mg capsules of the following composition were prepared:

| | |
|---|---|
| N-(1'-ethyl-2'-oxo-5'-pyrrolidinylmethyl)-2-methoxy-5-sulfamoyl benzamide | 50 mg |
| Lactose | 80 mg |
| Magnesium stearate | 10 mg |
| Sodium laurylsulfate | 1 mg |
| Talc | 9 mg |

EXAMPLE 4

An injectable sterilized ampoule of the following composition was prepared:

| | |
|---|---|
| N-(1'-ethyl-2'-oxo-5'-pyrrolidinylmethyl)-2-hydroxy-5-sulfamoyl benzamide | 100 mg |
| Propylene glycol isopropyl ether sufficient for an ampoule of sterile solution | 2 ml |

EXAMPLE 5

2 g suppositories of the following composition were prepared:

| | |
|---|---|
| N-(1'-ethyl-2'-oxo-5'pyrrolidinylmethyl)-2-methoxy-5-sulfamoyl benzamide | 100 mg |
| WITESPOL ® (glyceric ester of fatty acids) | 1.9 g |

The pharmaceutical preparations containing the benzamide compound or derivative thereof may be administered to patients in the daily dosage range of between about 50 mg and 2 g, depending upon the seriousness of the case. In all cases studied a remarkable improvement was observed following the initiation of treatment, including reduced psychic disturbances, resumption of almost normal activity and reduction of gastric disturbances. The pharmaceutical preparations may be used for both long and short term therapeutic treatment.

Pharmaceutical tests run on mice demonstrated the advantages of the benzamide compounds and their derivatives in treating psychic disturbances. Tests on mice of the type disclosed in the following literature demonstrated the ability of the benzamide compounds and their derivatives to modify behavior by action on the central nervous system:

Spontaneous motility of mice—P. Dews, *Brit. J. Pharmacol.* (1953)-8-46–48

Turning rod test—Kinnard and Carr, *J. Pharmacol. Exp. Ther.* (1957) 131-130–140.

The benzamide compounds and their derivatives were found to have a very low toxicity making them entirely compatible for therapeutic use without danger of secondary affects. Large dosages could be administered to mice without being lethal. For example, the administration of N-(1'-ethyl-2'-oxo-5'-pyrrolidinylmethyl)-2-methoxy-5-sulfamoyl benzamide gave the following results:

$LD_{50}/IV = 409$ mg/kg

Per os: no mortality at 3 g/kg.

We claim:

1. A substituted N-(1'ethyl-2'-pyrrolidinylmethyl) benzamide compound of the formula:

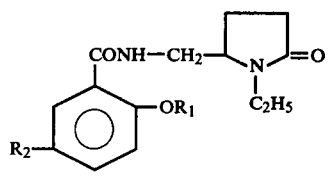

(I)

wherein:
R$_1$ is hydrogen or methyl and
R$_2$ is hydrogen or sulfamoyl,
a pharmacologically acceptable organic or inorganic acid addition salt, an alkyl ammonium salt, an N-oxide and an optical isomer thereof.

2. The compound of claim 1 wherein said benzamide is N-(1'-ethyl-2'-oxo-5-pyrrolidylmethyl)-2-methoxy-5-sulfamoyl benzamide.

3. The compound of claim 1 wherein said benzamide is N-(1'-ethyl-2'-oxo-5'-pyrrolidylmethyl)-2-hydroxy-5-sulfamoyl benzamide.

4. The compound of claim 1 wherein said benzamide addition salt is the salt of an acid selected from the group consisting of hydrochloric acid, hydrobromic acid, sulfuric acid, phosphoric acid, oxalic acid, acetic acid, tartaric acid, and methane sulfonic acid.

5. The compound of claim 1 wherein said benzamidequaternary ammonium salt is a salt of an alkyl sulfate or alkyl halide.

6. A pharmaceutical composition for the treatment of psychic disturbances, comprising (a) a substituted N-(1'-ethyl-2'oxo-5'pyrrolidinyl-methyl) benzamide compound of the formula:

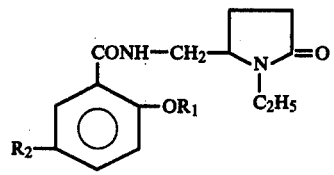

(I)

wherein
$R_1$ is hydrogen or methyl and
$R_2$ is hydrogen or sulfamoyl,
a pharmacologically acceptable organic or inorganic acid addition salt, an alkyl quaternary ammonium salt, an optical isomer thereof; and
(b) a pharmaceutically acceptable support therefor;
(c) said benzamide compound being present in an amount sufficient for the effective treatment of said psychic disturbances.

7. The pharmaceutical composition of claim 6 wherein said benzamide is N-(1'-ethyl-2'oxo-5'-pyrrolidylmethyl)-2-methoxy-5-sulfamoyl benzamide.

8. The pharmaceutical composition of claim 6 wherein said benzamide is N-(1'ethyl-2'-oxo-5'-pyrrolidylmethyl)-2-hydroxy-5-sulfamoyl benzamide.

9. The pharmaceutical composition of claim 6 wherein said benzamide compound is present in an amount between 50 and 200 mg.

10. The pharmaceutical composition of claim 9 wherein said benzamide compound is present in an amount between 50 and 100 mg.

* * * * *

UNITED STATES PATENT OFFICE
CERTIFICATE OF CORRECTION

Patent No. 4,161,532     Dated July 17, 1979

Inventor(s) Gerard Bulteau, Jacques Acher and Jean C. Monier

It is certified that error appears in the above-identified patent and that said Letters Patent are hereby corrected as shown below:

CLAIM 1:

Column 4:   Line 48, cancel "N-(1'ethyl-2'-pyrrolidinylmethyl)"

and substitute therefor:

-- N-(1'ethyl-2'-oxo-5'-pyrrolidinylmethyl) --

Line 64, after "alkyl" insert -- quaternary --.

Signed and Sealed this

Tenth Day of June 1980

[SEAL]

*Attest:*

SIDNEY A. DIAMOND

*Attesting Officer*     *Commissioner of Patents and Trademark.*